US008877894B2

(12) United States Patent
Rouvinen et al.

(10) Patent No.: US 8,877,894 B2
(45) Date of Patent: Nov. 4, 2014

(54) MODIFIED BETA-LACTOGLOBULINS FOR IMMUNOTHERAPY OF MILK ALLERGY

(75) Inventors: Juha Rouvinen, Joensuu (FI); Kristiina Takkinen, Espoo (FI); Merja Niemi, Joensuu (FI); Sirpa Jylhä, Espoo (FI); Hans Söderlund, Espoo (FI); Marja-Leena Laukkanen, Espoo (FI)

(73) Assignee: Teknologian Tutkimuskeskus VTT, VTT (FI)

( * ) Notice: Subject to any disclaimer, the term of this patent is extended or adjusted under 35 U.S.C. 154(b) by 157 days.

(21) Appl. No.: 12/999,955

(22) PCT Filed: Jun. 18, 2009

(86) PCT No.: PCT/FI2009/050549
§ 371 (c)(1),
(2), (4) Date: Jan. 4, 2011

(87) PCT Pub. No.: WO2009/153414
PCT Pub. Date: Dec. 23, 2009

(65) Prior Publication Data
US 2011/0104190 A1 May 5, 2011

(30) Foreign Application Priority Data
Jun. 18, 2008 (FI) .................................. 20085601

(51) Int. Cl.
*C07K 14/00* (2006.01)
*G06G 7/58* (2006.01)
*A61K 39/36* (2006.01)
*C07K 14/47* (2006.01)
*A61K 39/35* (2006.01)

(52) U.S. Cl.
CPC ............. *A61K 39/36* (2013.01); *C07K 14/4717* (2013.01); *A61K 39/35* (2013.01)
USPC ........................................... 530/350; 703/11

(58) Field of Classification Search
None
See application file for complete search history.

(56) References Cited

U.S. PATENT DOCUMENTS

2003/0064063 A1 4/2003 Saxon
2006/0216314 A1* 9/2006 Westritschnig et al. ... 424/275.1

FOREIGN PATENT DOCUMENTS

EP 1 403 280 A1 3/2004
JP 8-70866 A 3/1996

OTHER PUBLICATIONS

Moon et al., "A synergistic approach to protein crystallization: Combination of a fixed-arm carrier with surface entropy reduction", Protein Science, 2010, 19:901-913.*
McPherson, A. Current Approaches to Macromolecular Crystallization. European Journal of Biochemistry. 1990. vol. 189, pp. 1-23.*
Kundrot, C.E. Which Strategy for a Protein Crystallization Project? Cellular Molecular Life Science. 2004. vol. 61, pp. 525-536.*
Benevenuti et al., Crystallization of Soluble Proteins in Vapor Diffusion for X-ray Crystallography, Nature Protocols, published on-line Jun. 28, 2007, 2(7):1633-1651.*
Cudney R. Protein Crystallization and Dumb Luck. The Rigaku Journal. 1999. vol. 16, No. 1, pp. 1-7.*
Drenth, "Principles of Protein X-Ray Crystallography", 2nd Edition, 1999 Springer-Verlag New York Inc., Chapter 1, p. 1-21.*
Sakurai et al., "Manipulating Monomer-Dimer Equilibrium of Bovine _-Lactoglobulin by Amino Acid Substitution", The Journal of Biological Chemistry, vol. 277, No. 28, Issue of Jul. 12, pp. 25735-25740, 2002.*
de Halleux et al., "Three-dimensional structure and IgE-binding properties of mature fully active Der p 1, a clinically relevant major allergen," J. Allergy Clin. Immunol., vol. 117, pp. 571-576, 2006.
Ghosh et al., "Structural insight into Protein T1, the non-allergenic member of the Bet v 1 allergen family—An in silico analysis," Molecular Immunology, vol. 45, pp. 456-462, 2008, available online Jul. 20, 2007.
International Search Report issued Sep. 17, 2009, in PCT International Application No. PCT/FI2009/050549.
Niemi et al., "Molecular Interactions between a Recombinant IgE Antibody and the Beta-Lactoglobulin Allergen," Structure, vol. 15, pp. 1413-1421, Nov. 2007.
Ramos et al., "Recombinant Proteins and Peptides as Diagnostic and Therapeutic Reagents for Arthropod Allergies," Protein & Peptide Letters, vol. 14, pp. 992-1002, 2007.
Scholl et al., "Dimerization of the Major Birch Pollen Allergen Bet v 1 is Important for its In Vivo IgE-Cross-Linking Potential in Mice," The Journal of Immunology, vol. 175, pp. 6645-6650, 2005.
Search Report issued Mar. 12, 2009, in Finnish Patent Application No. 20085601.
Verdino et al., "The cross-reactive calcium-binding pollen allergen, Phl p 7, reveals a novel dimer assembly," The EMBO Journal, vol. 21, No. 19, pp. 5007-5016, 2002.
Li et al,, "Crystal Structure of a Dimerized Cockroach Allergen Bla g 2 Complexed with a Monoclonal Antibody", J. of Biological Chemistry, vol. 283, No. 33 (2008) pp. 22806-22814.

* cited by examiner

*Primary Examiner* — Suzanne M Noakes
(74) *Attorney, Agent, or Firm* — Birch, Stewart, Kolasch & Birch, LLP (57) ABSTRACT

The present invention is related to field of allergic (hypersensitivity) diseases and provides a method for producing modified allergenic polypeptides for use in immunotherapies. In the method of the invention, said allergenic polypeptides are modified so that they are not capable to form transient dimers. The invention also provides modified β-lactoglobulins for use in immunotherapy of milk allergy.

10 Claims, 9 Drawing Sheets

| Allergen type | Allergen source | Allergen | PDB-code | Monomer-monomer interface [Å2] | Designed hypoallergenic mutations |
|---|---|---|---|---|---|
| foods | cow's milk | Bos d 5 | 1BEB | 528 | H146P,R148P,S150P,I29K,D33K,D33E |
| tree fagales | birch pollen | Bet v 1 | 1BV1 | 822 | N28K,N28R,D25K,D25R,N47Y,N47W |
| tree fagales | birch pollen | Bet v 2 | 1CQA | 525 | A81V,A81Y,A83V,A83Y,A83R,A80K |
| animals | horse | Equ c 1 | 1EW3 | 1025 | F127K,F127R,V125K,V125R,V108K,V108R |
| insects | honey bee | Api m 1 | 1POC | 496 | M86K,M86R,F82K,F82R,I1Y,Y3K |
| grass poales | timothy | Phl p 1 | 1N10 | 1368 | I11K,I11R,A13Y,G8T,F217K,F189R |
| mites | house dust mite | Der p 1 | 1AS8 | 618 | N168Y,H72W,H72V,Y165E,Y165P,G164T |
| mites | house dust mite | Der p 2 | 1KTJ | 673 | Y75K,Y75R,N93Y,N93K,N93R,T91Y |
| animals | cat | Fel d 1 | 2EJN | 1239 | Y135K,Y135R,F85E,F85D,L132R,L132E |
| foods | celery | Api g 1 | 1BK0 | 569 | V105Y,V105E,K115R,V103Y,V103R,A78P |
| weed | lamb's quarters | Che a 3 | 2OPO | 303 | R49Y,G59K,G59T,A53Y,F62K,F82R |
| insects | honey bee | Api m 4 | 2MLT | 590 | S18Y,S18K,S18R,P14K,P14E,T37Y |

Figure 4 ptac: promoter
SSpelB: signal sequence of pectate lyase of *Erwinia carotovora*
6 x His: C-teminal hexahistidinyl tag
TT: transcription terminator

MODIFIED BETA-LACTOGLOBULINS FOR IMMUNOTHERAPY OF MILK ALLERGY

FIELD OF THE INVENTION

The present invention is related to field of allergic (hypersensitivity) diseases and particularly to protein engineering technology for producing modified allergenic polypeptides (hypoallergens) for use in immunotherapies.

BACKGROUND OF THE INVENTION

Allergic diseases, for example, asthma, rhinitis, eczema and food allergies are reaching epidemic proportions in the world. These type I hypersensitive reactions are based on the formation of immunoglobulin E (IgE) antibodies against, in principle, harmless antigens, allergens.

Immunoglobulin E molecules are produced by B cells. Each immature B cell expresses a monomeric form of IgM on its surface but all these antibodies are identical in amino acid sequence, and hence, in antigen-binding specificity. By binding to IgM antibodies the foreign multivalent antigen crosslinks B-cell (Igα/Igβ) receptors on the immature B cell surface. This triggers B-cell proliferation, differentiation into antibody-producing plasma cells, memory formation, and antigen presentation to T cells. T cells provide help for the B cells to mature which includes both isotype switching and activation of somatic mutations to improve secreted antibody affinity and selectivity. It has been observed that in allergy T helper cells differentiate to Th2 cells which produces cytokines (IL-4 and IL-13) which cause the isotype switching from IgM to IgE antibody (antibody heavy chain type is changed from μ to ε; light chain type is not changed) (Alam et al., 2003; Chaplin 2003).

The mature B cell is then able to secrete IgE antibodies which are able to bind both to antigens (allergens) but also to high affinity FcεRI receptors on a mast cell or basophil surface. The crosslinking of FcεRI complexes on the cell surface triggers the granulation of biological mediators like histamine and lipid mediators that cause inflammatory reactions (Prussin et al., 2003).

As previously described, the crosslinking of cell-surface receptors appear in two stages. Firstly, when antigen (allergen) crosslinks Igα/Igβ receptors on the immature B cell surface, and secondly, when allergen crosslinks FcεRI receptors on the mast cell surface. In addition, similar crosslinking occurs on the activation of antigen-presenting cells (APCs) like dendritic cells (Gould et al. 2008). In these cases, crosslinking is possible, when antigen (allergen) is multivalent, having multiple binding sites (epitopes) for antibodies.

The first three-dimensional immunocomplex structure of allergen and IgE antibody was recently published (Niemi et al., 2007). In this structure, dimeric β-lactoglobulin (BLG) from cow's milk (Bos d 5) is bound to two IgE/Fab fragments. Surprisingly, the IgE-binding epitope of BLG covered a flat area on the allergen surface which is unusual because according to the crystal structures the majority of known IgG epitopes are located in the protruding areas of antigens. The IgE/Fab fragments were located on the same side which makes, in principle, possible that dimeric BLG is able to link two identical IgE antibodies leading to the mast cell granulation.

This novel observation about the role of dimerization for the allergenicity of BLG lead the inventors further to investigate how common dimerization (or other type of oligomerization) is among allergens. Some allergens were reported to be oligomeric but most allergens were reported to be monomeric. It was also soon realized that there are controversial data in the literature. In corresponding cases, such as reports considering birch allergen Bet v 1, the allergen was reported to exist as monomer and sometimes as dimer. In fact, BLG is a well studied example of a transient dimer, a protein which may exist both as monomer or dimer in solution (Nooren et al., 2003). Sakurai and Goto (2002) have also studied the monomer-dimer equilibrium of BLG as a model of protein-protein interaction. Thermodynamically, the dissociation constant for the dimer is so high that in solution, BLG may exist both as monomer and dimer. Naturally, environmental factors, like pH or salt concentration affect on equilibrium. However, in physiological conditions in the body BLG is almost totally monomeric. The key element of the present invention is that transient dimerisation in many cases is a critical feature of allergens, and this transient dimerisation can be obstructed by directed mutagenesis.

Transient dimers are difficult to observe because high dissociation constant for dimer reduces the dimeric fraction to negligible at normal cellular concentrations (10-100 nM). However, by colocalization within a cell may increase concentration locally (to 1 mM), and the interaction between monomers can increase from neglible to substantial (Kuriyan et al., 2007). One example of the colocalization is the binding of antigens (allergens) on the surface of immature B cell or mast cell. This would mean that weak homodimerization of allergen on the cell's surface may be enough for signal transduction leading to sensitization or allergic reaction. The significance of allergen dimerization has previously been studied very little. Scholl et al. has studied the role of dimerization of birch pollen allergen Bet v 1 for cross-linking. Skin tests in Bet v 1-allergic mize were positive with Bet v 1 dimer, but remained negative when using the monomer. In addition, the monomer was less capable of activating murine memory B cells for IgE production in vivo. In this study, monomeric form of Bet v 1 was prepared with the addition of 4% glycerol (Scholl et al., 2005). However, the problem is that the effect of additive is only temporary because glycerol is gradually diluted and the normal monomer/dimer equilibrium is reached. Later, according to the molecular modelling analysis it was suggested that nonallergenicity of T1 protein, a member of Bet v 1 protein family was possibly based on prevented dimerization of T1 protein (Ghosh D et al., 2008). Verdino et al suggested in 2002 that the disruption of the dimer assembly of Phl p 7 allergen would diminish cross-linking. However, in the case of Phl p 7 it is in practise very difficult to create stable monomeric variant, because two polypeptide chains are very strongly associated together forming a very stable dimer (Verdino et al. 2002).

The influence of quaternary structure to allergenicity and immunogenicity of cockroach allergen Per a 3 has also been investigated. Hexameric form induced a stronger leukotrience release from basophils than the monomeric form. Unfortunately, the preparation of monomeric and hexameric forms of Per a 3 was not described in the paper (Bellinghausen et al., 2007). Another study of cockroach allergen Bla g 2 showed that dimeric wild type Bla g 2 induced more β-hexosaminidase release from mast cells than a monomeric Bla g 2 mutant (Li et al. 2008). However, the authors concluded that Bla g 2 would exist as a dimer in physiological conditions.

In de Halleux et al., 2006, it is disclosed that it is expected that a monomeric form of Der p 1 would be less prone to trigger anaphylactic reactions on injection to sensitized patients. However, experiments showing such results are not disclosed.

BRIEF DESCRIPTION OF THE DRAWINGS

FIG. 1 shows examples of symmetric allergen dimers found in the crystal structures drawn in the same scale. One monomer is shown as a light grey ribbon model, the second monomer as a dark grey ribbon model. The dimeric allergen is shown in two orientations. In the left picture the symmetric two-fold axis is towards viewer, in the right picture the axis is in the same plane than the paper. The picture in the upper left corner shows the crystal structure of BLG-D1/IgE(Fab) (Bos d 5) immunocomplex in which IgE fragments are shown as grey surface models. The coordinates for the allergens were obtained from the protein data bank and the coordinates for the dimers were created with the PISA-server. The figure was created by PYMOL program (DeLano 2002). Che a 3 contains four polypeptide chains. Two of polypeptide chain form an obligate dimer (two monomers form together the compact structure; monomer can not form a stable structure alone (Nooren et al., 2003)). Two obligate dimers form a transient dimer. Api m 4 contains eight polypeptide chains. Four of them form a stable obligate tetramer. Two of tetramers form a transient structure. Other examples represent transient dimer structures in which monomer unit consists of a single polypeptide chain.

ABBREVIATIONS

BLG β-lactoglobulin
cDNA complementary deoxyribonucleic acid
DNA deoxyribonucleic acid
*E. coli* Escherichia coli
EIA enzyme immunoassay
ELISA enzyme-linked immunosorbent assay
Fab fragment with specific antigen binding
IgG immunoglobulin G
IgE immunoglobulin E
IgM immunoglobulin M
NMR nuclear magnetic resonance
PCR polymerase chain reaction

DETAILED DESCRIPTION OF THE INVENTION

As described above, the capability to form dimers or oligomers seems to have a significant role for immunogenicity (B-cell activation) and allergenicity (mast cell, basophil triggering) of allergens. If the formation of stable or even transient symmetric homodimers is reduced and allergen would exist only in monomeric form, this would offer a basis to develop a new generation of hypoallergens: monomeric allergens. The monomeric variants would have advantageous properties when considering specific immunotherapy. The monomeric allergens would not trigger mast cell or basophil degranulation. In addition, monomeric variants would bind allergen specific IgE antibodies preventing the binding of native allergens. This would make it possible to use larger amounts of monomeric variants as allergy vaccine to induce production of protective IgG antibodies, or to compete with natural allergens. It would also make it possible to reduce the binding of natural dimeric allergens to mast cells or basophils by competition based on a higher concentration of the hypoallergic monomeric allergens which do not cause the formation of crosslinked FceRI complexes Therefore, based on this discovery of the significance of dimerization, particularly transient dimerization, in allergenicity the object of the invention is to provide a method for preparing a hypoallergen for immunotherapy. The method comprises the steps of:

a) checking a known allergenic polypeptide for surface structures related to the formation of dimers or oligomers, i.e. a monomer-monomer interface, or if the surface area for dimer or oligomer formation is already known, directly employing step (b);

b) altering the surface area of said polypeptide discovered or suspected to be related to the formation of dimers or oligomers in order to inactivate or reduce the polypeptide's natural ability to form dimers or oligomers; and c) testing the altered polypeptide obtained from step b) for ability to activate histamine release or other mediators of an allergic reactions from human cells, wherein those altered polypeptides which do not activate histamine release or said other mediators or activate histamine release or said other mediators less than the parent polypeptide are considered as hypoallergen candidates for immunotherapy.

The method may further comprise a step of checking that a IgE antibody specific to said allergenic polypeptide still binds to the altered polypeptide obtained from step b) or c) to confirm that said allergenic polypeptide has a native-like structure, capability to block IgE antibodies and immunogenic potential to develop protective IgG antibodies.

The method may also comprise a step of administering a pharmaceutically effective amount of the altered polypeptide obtained from step b) or c) to a patient suffering from an allergy. The altered polypeptide may be mixed with pharmaceutically acceptable carriers and diluents for use in immunotherapy of an allergy.

Thus, the present invention is also directed to the use of monomeric variants of allergens (such as modified β-lactoglobulins having the sequence selected from the group consisting of SEQ ID NOS:1-4) in immunotherapy. The term immunotherapy as used herein defines at least three modes of treatments:

a) desensitization therapy by using over time multiple doses of low concentration of monomeric variants of allergens;
b) using a few doses of relatively high concentrations of monomeric variants to induce an IgG response towards the native allergen (i.e. an allergy vaccination scheme); and
c) using the monomeric variant as a therapeutic to cure allergy symptoms by competing the native allergen for binding to IgE.

The present invention is specifically directed to a modified β-lactoglobulin obtained by the method of the present invention and having the sequence selected from the group consisting of SEQ ID NOS:1-4 or to the use thereof for the manufacture of a pharmaceutical composition or vaccine for the treatment of milk allergy.

The present invention is also directed to method of treatment of milk allergy wherein pharmaceutically effective amount of the hypoallergen is administered to a patient in need of said treatment.

Pharmaceutical compositions or vaccines comprising said hypoallergens can be prepared for storage by mixing the protein having the desired degree of purity with optional physiologically acceptable carriers, excipients, or stabilizers in the form of lyophilized cake or aqueous solutions. Acceptable carriers, excipients, or stabilizers are non-toxic to recipients at the dosages and concentrations employed, and include buffers such as phosphate, citrate, and other organic acids.

The hypoallergen may also be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nanoparticles, and nanocapsules), or in macroemulsions.

The route of hypoallergen administration is in accordance with known methods, e.g., topical, oral or the general routes of injection or infusion by intravenous, intraperitoneal, intracerebral, intramuscular, intraocular, intraarterial, or intralesional means. Administration can be continuous or periodic.

Transient Dimers

There is no published experimental study about transient dimer formation of allergens. However, it is possible to evaluate frequency of transient dimers by looking available crystal structures. In a typical crystallization experiment the concentration of protein is about 10 mg/ml which corresponds 0.5 mM concentration for 20 kDa protein. This would increase the fraction of possible dimeric form of protein considerably. However, it should be noted that crystallization solution contains also monomeric fraction which may crystallize. In addition, very high or low pH, precipitants and additives may affect crystallization. For transient dimers, the area of dimer interface is preferably about or under 850 Å$^2$, since for those dimers which are predicted to be transient, the area is 530 Å$^2$ (BLG), 620 Å2 (Der p 1) or 820 Å$^2$ (Bet v 1). Stronger dimers seem to have much larger dimer interfaces, such as 1139 Å$^2$ for Bla g 2.

Therefore, as described above, the expression "transient dimers" means that:
 a) dimerisation of allergens is concentration dependent, at physiological concentrations (10-100 nM) they exist essentially as monomers;
 b) co-localization mediated increase of local concentration is needed for in vivo dimerization; upon binding to IgE-FcεRI receptor complexes on mast cells or basophils monomeric allergens form transient dimers;
 c) in transient dimers the monomeric subunits are not covalently linked and the monomeric subunits are able to fold independently; and
 d) surface area of the monomer-monomer interface of transient dimers area is relatively small (less than 850 Å$^2$).

The Protein Data Bank (www.rcsb.org) contains at this moment (February 2008) the coordinates for 54 allergen structures. Nine structures have been determined by using NMR and these can not be used in the evaluation. The remaining 45 allergen structures were studied by using PISA server from European Bioinformatics Institute (www.ebi.ac.uk/msd-srv/prot_int/pistart.html) (Krissinel E et al., 2007). PISA uses the crystal data to predict oligomeric state (quaternary structure) and it can be used also to evaluate protein-protein interfaces. PISA is able to predicts well the structure of stable dimers. However, because of smaller monomer-monomer interface, it predicts that BLG would be monomeric.

However, PISA is useful in this study because it gives protein-protein interfaces. In principle, it is difficult to distinguish dimeric interface from crystal contacts. However, true homodimeric complexes are almost always symmetrical, there exist rotational symmetry axis between monomers (Blundell et al., 1996). PISA server can be used to search for interfaces and find possible rotational symmetry axis between monomers.

Figure 1:
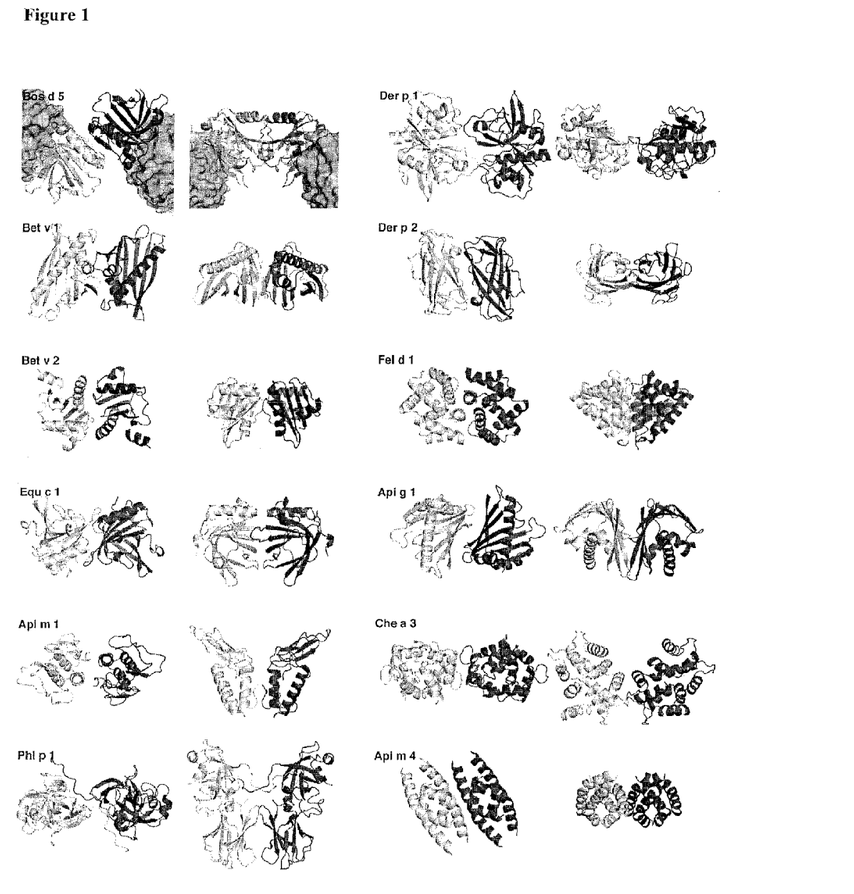

We have analyzed 45 allergen crystal structures. 35 allergens (78%) existed in the crystal forms in which allergens were found to form symmetric homooligomers, mainly dimers. Two of the symmetric dimers were very weak. However, the fraction of homooligomers among allergens was very high giving evidence that the capability to form oligomers is very common property among allergens. Some of the found dimers of allergens are shown in FIG. 1. Ten allergens were found to exist in monomeric form in crystals.

Detecting Monomer-Monomer Interfaces and Design of Hypoallergenic Mutations

1) If no three-dimensional structure of the allergen of interest is available, then i) the allergen is crystallized, ii) its structure is determined by using X-ray diffraction, and iii) the coordinates of the solved three-dimensional crystal structure is used to analyze visually allergen molecule packing by using molecular graphics software (like PYMOL (DeLano 2002), O (Jones et al. 1991), and XTALVIEW (McRee, 1999)). Alternatively, computer programs such as PISA (Krissinel et al. 2007; http://www.ebi.ac.uk/msd-srv/prot_int/pistart.html) can be used to analyze allergen molecule packing in the crystal. In the analysis, the goal is to find rotational symmetry axis between allergen molecules. In the most cases it is a two-fold symmetry axis. (An object that can be rotated about an axis and repeats its form at least once during the rotation is said to have an axis of rotational symmetry. The axis along which the rotation is performed is an element of symmetry referred to as a rotation axis. An object that appears identical after a rotation of 180°, that is twice in a 360° rotation, is said to have a 2-fold rotation axis.) If rotational symmetry axis is found between monomers of an allergen, this is an indication that the allergen is able to form symmetrical homooligomer at least in high protein concentrations.

2. If the three-dimensional crystal structure is known it is possible to proceed directly to step iii) in 1).

3. When the axis has been found, the molecular graphics program such as PYMOL can be used to analyze monomer-monomer interface between allergen monomers. In Table 2, the area of detected monomer-monomer interfaces of numerous allergens is listed. In the next step, the monomer-monomer interface can be used to detect amino acid residues the substitution of which would hinder dimer formation. In FIG. 3, a list of suggested mutations to amino acids in monomer-monomer interfaces of different allergens is shown. Typical amino acid substitutions would be the mutation of small residues with larger ones. In addition, the hydrophobic residues (like phenylalanine or leucine) could be replaced by hydrophilic residues (glutamic acid, lysine). Other preferable substitutions are discussed below.

4. If rotational symmetry axis has not been found between monomers it is possible i) to crystallize allergen in a different crystal form (by using different crystallization conditions, for example, by changing pH, protein or precipitant concentration). Alternatively, monomers can be docked computationally together by using symmetrical restraints. This can be done by using ROSETTA software (Andre et al., 2007).

5. Preferably, the reduced capability of mutant proteins to form dimers will be tested, for example, by determining dissociation constant for dimer. However, it is important to check that the monomeric variant is folded like native protein retaining the binding properties to IgE antibodies.

Figure 9:
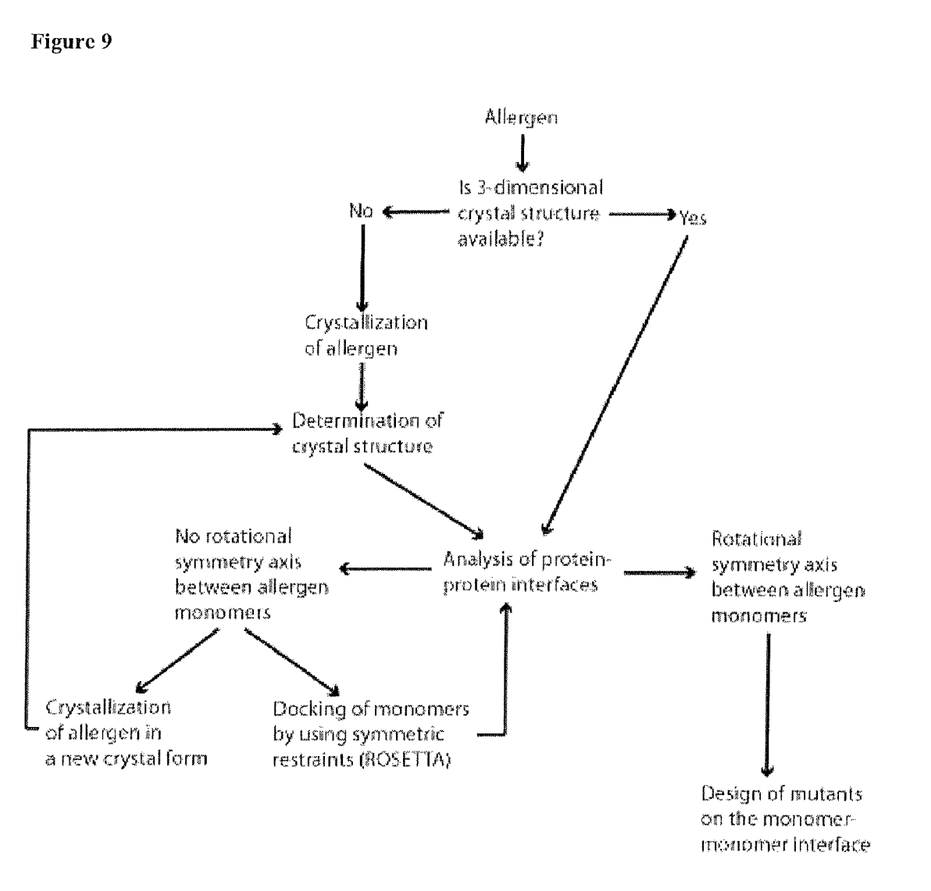
FIG. 9 shows a work flow chart for the search of monomer-monomer interfaces and design of hypoallergen mutants capable of preventing dimer formation.

6. In principle, if the three-dimensional structure of allergen is not known, residues of protein can also be randomly mutated. Again, the possible reduced dimer formation and the folding of the monomeric variant will be tested (see also FIG. 9).

Development of Monomeric Hypoallergens

Figure 2:
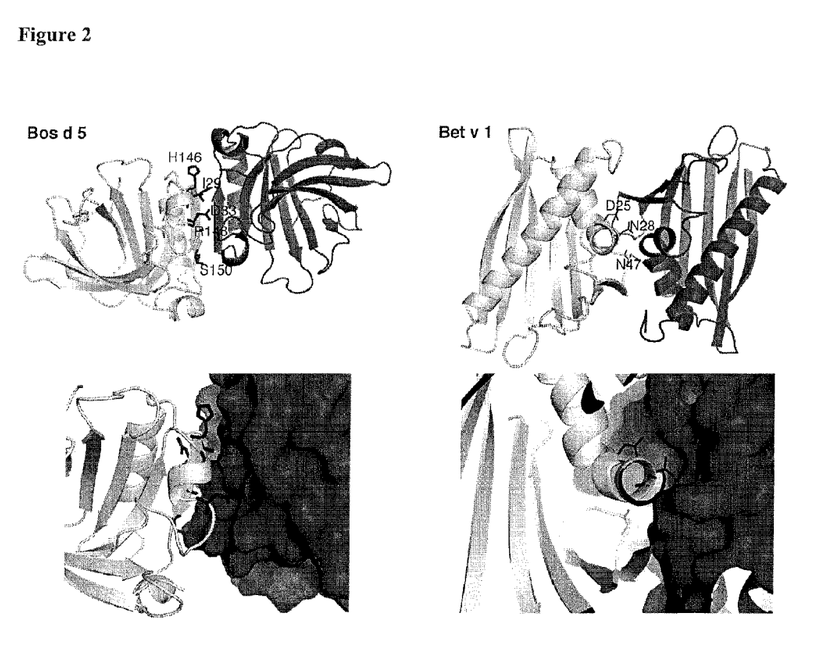
FIG. 2 shows the positions of designed mutants on the monomer-monomer interface of dimeric Bos d 5 (β-lactoglobulin) and Bet v 1 allergen. The figure was created with the PYMOL program.

The stable monomeric variant of allergen could be prepared by mutating amino acid residues on the dimer interface. As an example, monomer-monomer interface of BLG is shown in FIG. 2. The mutated amino acid residues in FIG. 3 (His 146, Arg 148, Ser 150) decrease dimeric and increase monomeric form of BLG in solution.

Preferably, monomeric variants can be obtained by mutating some (e.g. 1-5) amino acid residues on the surface related to dimer or oligomer formation into bulky residues (e.g. Arg, Tyr, Lys, Trp can be mutated to Ala or Pro). The mutated residues are preferably those which side chains are pointing outside towards solvent thus causing minimal change to the basic structure of the allergen. A person skilled in the art can easily alter the surface area of an allergenic polypeptide by applying conventional genetic engineering techniques. Mutations can be introduced to the nucleic acid encoding said polypeptide, e.g., by PCR-based methods and other methods for directed mutagenesis as well as by random mutagenesis or by full sized synthetic genes. These methods are well-known in the art (see, for example, Current Protocols in Molecular Biology, eds. Ausubel et al, John Wiley & Sons: 1992).

Histamine Release Assay

Histamine is an important mediator in an "immediate type" allergy after allergen administration and is found in the initial phase of an anaphylactic reaction. Therefore, the potential of hypoallergens for immunotherapies can easily be tested by different histamine release assays.

The hypoallergens of the present invention have reduced allergenic activity compared to corresponding wild type allergens. According to the invention the term "allergenic activity" denotes the capability of a compound or composition to induce an allergic reaction in a sensitized mammal, e.g. in a milk-allergic patient. An allergic reaction may be mast cell degranulation, positive skin reaction and/or nasal reaction. The allergenic activity is preferably defined in suitable in vitro or in vivo tests. The allergenic activity may be determined in a skin prick test as described in van Hage-Hamsten et al. (1999) or in Pauli et al. (2000).

Preferably, the allergenic activity of the hypoallergen is less than 50% of the allergenic activity of the wild type allergen. More preferably, the allergenic activity of the hypoallergen is less than 25% of the wild type allergen. In the most preferred embodiment the hypoallergen has substantially no allergenic activity. Generally, the histamine release induced by the hypoallergen of the invention is significantly reduced compared to the histamine release induced by the corresponding wild type allergenic polypeptide. A preferred in vitro test for determining the histamine release is the basophil histamine release assay as described in Vrtala et al., (1997) (see also Example 3). Preferably, the histamine release is reduced by at least 25%, more preferably by at least 50%, most preferably by at least 75%, determined at that concentration of allergen at which the corresponding wild type allergen shows maximum histamine release.

The publications and other materials used herein to illuminate the background of the invention, and in particular, to provide additional details with respect to its practice, are incorporated herein by reference. The present invention is further described in the following example, which is not intended to limit the scope of the invention.

EXPERIMENTAL SECTION

Example 1

Detection of Monomer-Monomer Interface of β-Lactoglobulin

Based on Sakurai and Goto (2002) and confirmed by the three-dimensional immunocomplex structure of allergen and IgE antibody recently published by Niemi et al., 2007, the monomer-monomer interface of β-lactoglobulin has been shown to comprise, among others, amino acids Asp33, Ala34, Arg40, His146, Arg148 and Ser150.

Example 2

Characteristics of Recombinant Monomeric β-Lactoglobulin Mutants

In this example the recombinant monomeric β-lactoglobulin (BLG) mutants containing amino acid substitutions were constructed and their anti-BLG IgE antibody (D1) binding properties were characterised. Sakurai and Goto (2002) have studied the monomer-dimer equilibrium of BLG as a model of protein-protein interaction.

I. Construction of Monomeric β-Lactoglobulin Mutants

For the construction of monomeric BLG mutants the following amino acid substitutions were performed: H146P, R148P, S150P and H146P/R148P/S150P (triple mutant) (SEQ ID NOS:1-4). Previously the cDNA encoding the recombinant dimeric BLG was cloned into the bacterial expression vector pKKtac. The amino acid substitutions were subjected by PCR amplification using 5'-end primer A and 3'-end primers B-E (Table I). Primer B was used for H146P, primer C for R148P, primer D for S150 and primer E for H146P/R148P/S150P substitution. The PCR amplification was carried out using the "touch-down" conditions: first 2 min at 95° C. then 25 cycles of 1 min at 94° C. for denaturation, 30 s at 70° C. and decreasing 0.7° C. per cycle for annealing and 2 min at 70° C. for elongation followed by 20 cycles of 1 min at 94° C., 30 s at 55° C. and 2 min at 72° C. followed by 1 cycle of 10 min at 72° C.

Figure 4:
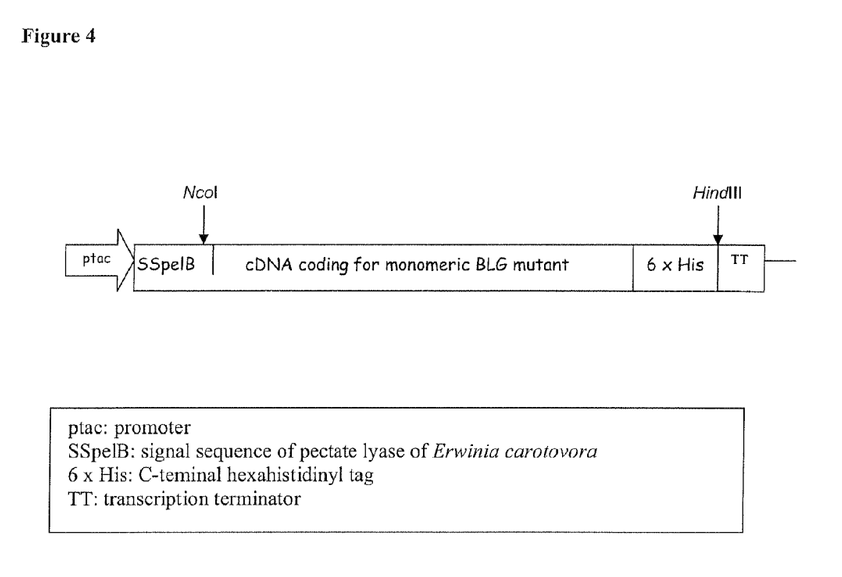
FIG. 4 shows a schematic presentation of the bacterial expression vector used for the construction and production of monomeric BLG mutants.

The resulting amplified cDNAs of the monomeric BLG mutants were cloned into the bacterial expression vector (pKKtac) using NcoI and HindIII cloning sites (FIG. 4) and then transformed into *E. coli* RV308. The monomeric BLG mutants containing C-terminal hexahistidinyl tag were bacterially produced in a large scale (1 liter) for the IMAC purification. Because the recombinant BLG mutants were secreted into the periplasmic space of *E. coli* but not to the culture media, the periplasms were isolated and then they were subjected onto a Sepharose column with immobilised nickel. The purified monomeric BLG mutants were with a substantial purity.

II. Characterisation of the Monomeric β-Lactoglobulin Mutants

The binding properties of the anti-BLG IgE antibody (D1) to the purified monomeric BLG mutants were analysed by competitive ELISA.

Figure 5:
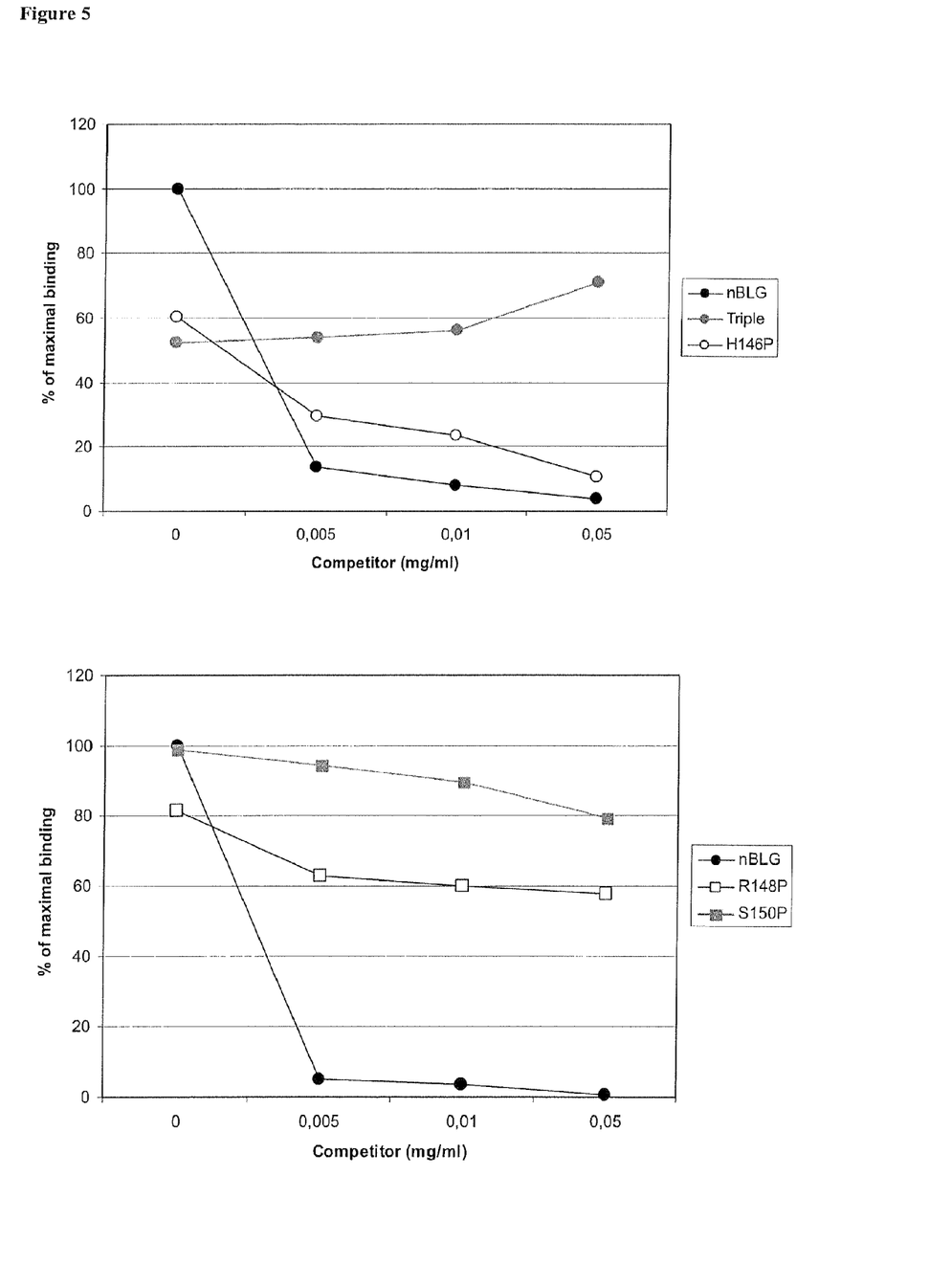
FIG. 5 shows the inhibition result obtained from the competitive ELISA of D1 IgE Fab fragment with human IgG1 subtype that binding to immobilised, biotinylated β-lactoglobulin has been inhibited by soluble native β-lactoglobulin as well as monomeric H146P, R148P and S150P BLG mutants.

First, increasing amounts of the non-biotinylated native BLG (nBLG) and monomeric BLG mutants were incubated with the D1 IgE Fab fragment, and then the reaction mixtures were applied onto Streptavidin microtitre plate wells coated with biotinylated BLG. FIG. 5 shows the result of the competitive ELISA. In the case of native BLG and monomeric H146P, R148P and S150P BLG mutants used as competitor the binding of the D1 IgE Fab to biotinylated β-lactoglobulin could be inhibited.

III. Circular Dichroism Measurements

Figure 6:
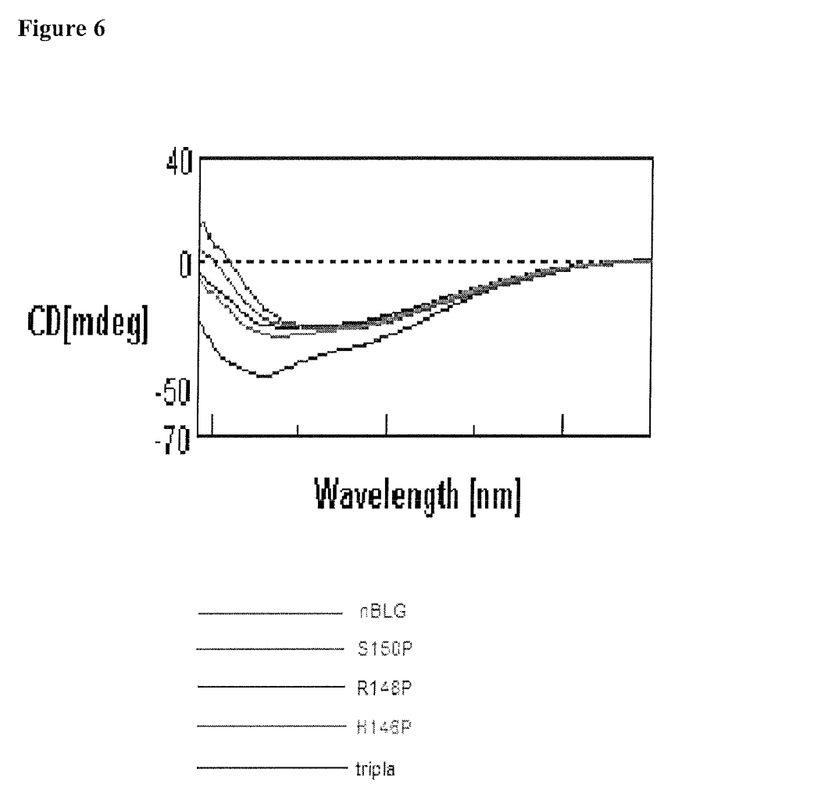
FIG. 6 shows the CD-spectra of the soluble native β-lactoglobulin as well as monomeric H146P, R148P and S150P BLG mutants.

Circular dichroism (CD) can be used to determining whether a protein is folded properly and further comparing structures for different mutants of the same protein. For circular dichroism (CD) measurements the buffer of all rBLGs was exchanged into 5 mM Hepes (pH 7.4) using dialysis. Far-UV spectrum of the native BLG (nBLG, Sigma), monomeric H146P, R148P and S150P BLG mutants was measured with Jasco J-715 spectropolarimeter at +20° C. controlled with a Peltier thermostat (Jasco PTC-348WI) using a 1-mm quartz cell. The concentrations of the proteins were 1 mg/ml for nBLG, 0.50 mg/ml for H146P, 0.20 mg/ml for R148P and 0.23 mg/ml for 5150 BLG mutant. The CD-spectra shown are averages of three measurements (FIG. 6). According to CD spectra the recombinant monomeric BLG mutants (except the triple mutant) show similar structure compared to the native BLG (nBLG).

Example 3

Functionality of Monomeric BLG Mutants for Histamine Release

The induction of the in vitro release of histamine from basophilic leukocytes by nBLG and monomeric BLG mutants was analysed by histamine release EIA using stripped and sensitized basophils followed by histamine ELISA (LD-BA).

Whole blood (25 ml) from non-milk allergic donor was used for the isolation of the leucocytes. The red blood cells were lysed by mixing them with a lysis buffer (155 mM $NH_4Cl$, 10 mM $NH_4HCO_3$, 0.1 mM EDTA, pH 7.4), incubating 15 min on ice and then centrifuging with 450×g for 10 min at RT. The supernatant was discarded and cell pellet was lysed again as above. Finally, the white cell pellet was washed once with sterile PBS and 0.9% NaCl (w/v) and the number of the cells was counted by haemocytometer. Then the bound IgE molecules were stripped off from the basophils by incubating them in a 5-ml stripping buffer (13.4 mM lactic acid, 140 mM NaCl, 5 mM KCl, pH 3.9) for 3.5 min. The stripped cells were washed with Hepes buffer [20 mM Hepes, 132 mM NaCl, 6 mM KCl, 1 mM $MgSO_4$, 1.2 mM $K_2HPO_4$, 5.5 mM glucose, 0.5% Human serum albumin (w/v, Sigma A3782), pH 7.4]. Finally, the cells were resuspended into 600 µl Hepes buffer and divided into two tubes: P3 (+) tube (400 µl) and negative control (−) tube (200 W). For the sensitization of the cells by milk allergic IgE serum they were incubated with the following sensitization mixture: 100 µl serum from a milk allergic P3 (+) or 50 µl serum non-allergic (−) donor, 4 mM EDTA in a total volume of 0.5 ml for 90 min at +37° C. After the sensitization, 2 ml Hepes buffer was added to the cells and they were washed twice with Hepes buffer. Cells were allowed to recover in Hepes buffer with 1 mM $CaCl_2$ for 30 min at +37° C. The sample volumes were adjusted with a Hepes buffer with 1 mM $CaCl_2$ as follows: P3 (+) cells 8 ml and negative control (−) cells 4 ml (approximately $2.2 \times 10^5$ cells/ml)

Histamine release assay was performed using Supplementary Kit for Histamine Release (Labor Diagnostika Nord GmbH & Co. KG, cat. No. BA 10-1100). For the total release of histamine 30 µl stripped and sensitized cells was mixed with 270 µl Release buffer and incubated for 10 min at 90° C. The samples were centrifuged for 10 min with 700×g and 50 µl of the supernatant was taken out for the acylation. For the allergen induced histamine release the allergens (nBLG, rBLG and its mutants) were diluted into the concentrations of 0.1 mg/ml, 0.01 mg/ml and 0.001 mg/ml into the Release buffer (Vtot=500 µl). Then 150 µl each allergen dilution and 150 µl cell suspension or 150 µl Release buffer and 150 µl cell suspension (for spontaneous release) or 150 µl anti-IgE antiserum (1 µg/ml) and 150 µl cell suspension (as positive control) were mixed and incubated for 60 min at +37° C. In order to stop the release reaction the samples were incubated for 10 min on ice and then centrifuged for 10 min with 700×g. For the acylation of the released histamine 50 µl of the clear supernatant was used.

The released histamine was measured by Histamine ELISA (Labor Diagnostika Nord GmbH & Co. KG, cat. No. BA 10-1000). In the ELISA the histamine was quantitatively derivatized into N-acylhistamine that was bound to the solid phase of the microtiter plate. Released and acylated histamine and solid phase bound acylhistamine competed for a fixed number of antiserum IgE binding sites. When the system was in equilibrium, free antigen and free antigen-antiserum complexes were removed by washing step. The antibody bound to the solid phase histamine was detected by peroxidise-conjugated anti-goat antibody. The substrate TMB/peroxidase reaction was monitored at 450 nm. The amount of antibody bound to the solid phase histamine was inversely proportional to the released histamine concentration of the sample. The acylation of the samples and the immunoassay were performed by following the manufacturer's instructions (Labor Diagnostika Nord GmbH & Co. KG, cat. No. BA 10-1000). The histamine concentrations of the samples were read directly from the standard curve and the result of the total histamine was multiplied by the factor 5. Regarding the total histamine concentration (100%) the allergen induced histamine concentrations were calculated in percent as well.

Figure 7:
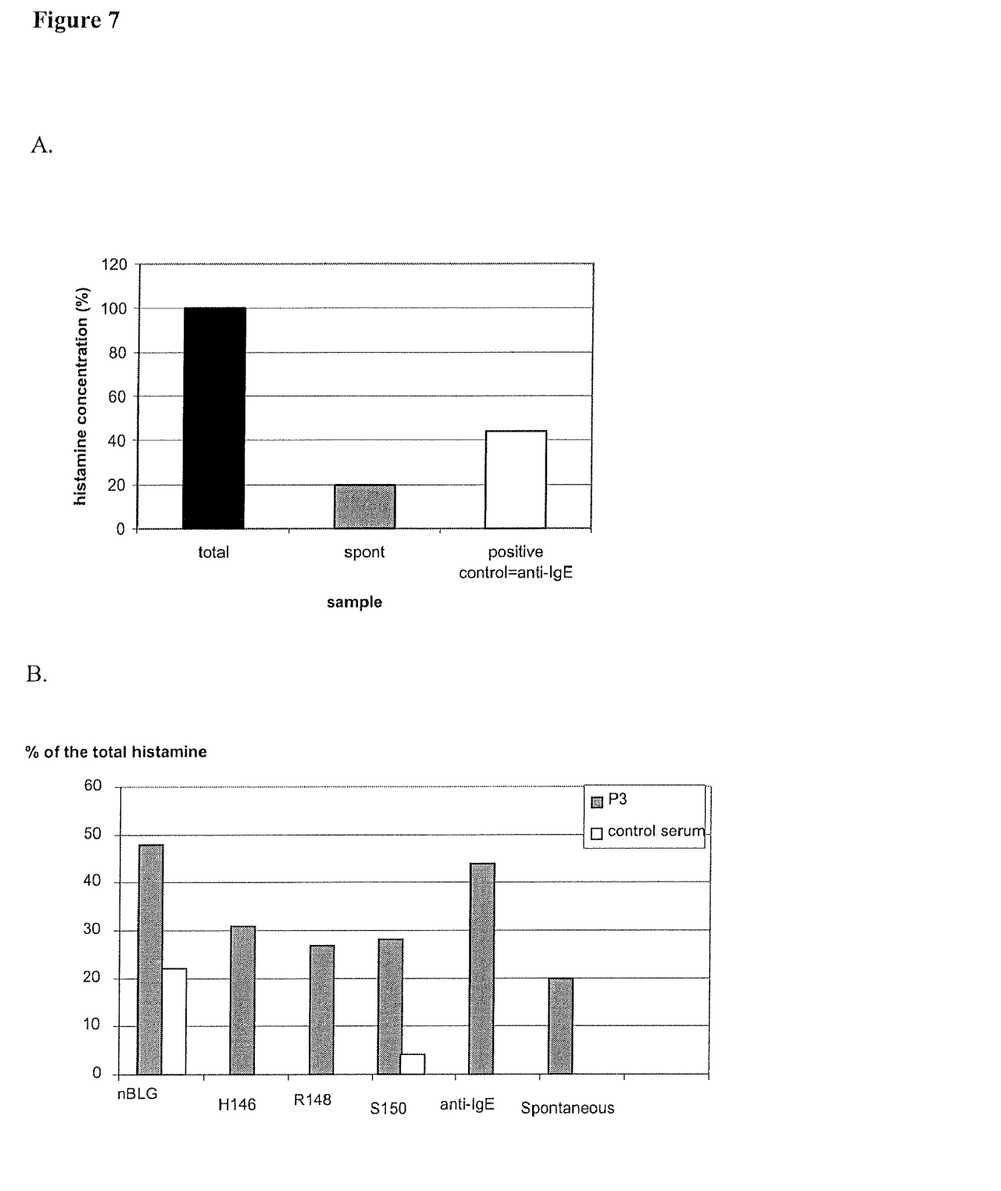
FIG. 7 shows the control samples (A) and allergen (BLG and its mutants)(B) derived histamine release from the stripped and sensitised basophils. According to manufacture's protocol the spontaneous release should give values<5% and the positive control sample>5% of total histamine release.
Figure 8:
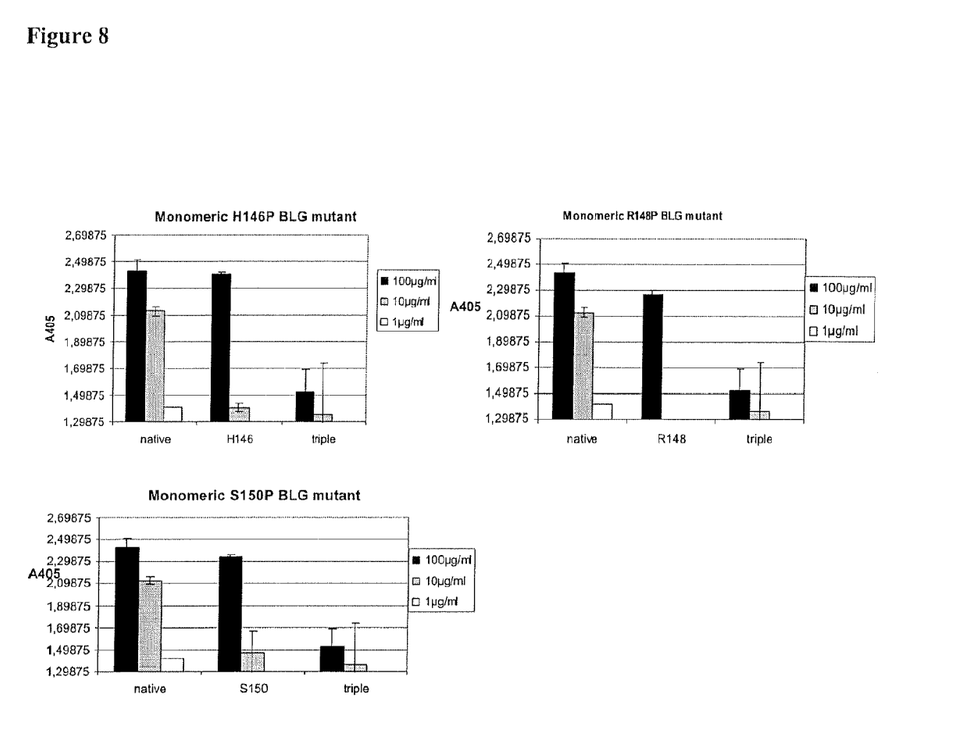
FIG. 8 shows the binding of the D1 Fab and D1 scFv to the dimeric BLG and its monomeric mutants analysed by ELISA.

FIG. 7 A shows that the overall condition of the cells used for the histamine release assay. According to manufacture's protocol the spontaneous release should give values<5% and the positive control sample>5% of total histamine release. The histamine release of the nBLG and the recombinant monomeric BLG mutants is shown in FIG. 7 B. The dimeric nBLG triggered the high-level histamine release whereas the monomeric mutants showed notably lower histamine release levels. These results demonstrate that monomeric BLG mutants behave in functional assay as expected.

Sandwich ELISA

Microtitre plate wells (Nunc) were coated with 1 µg anti-BLG D1 Fab for 16 hours at +4° C. For the prevention of the unspecific binding to the wells they were blocked with 200 µl 0.5% BSA-PBS for 1 h at room temperature. The BLGs (native or recombinant monomer mutants) were added to the wells at the concentrations 100, 10, and 1 µg/ml in 0.5% BSA-PBS and incubated for 1 h at room temperature. After washing step anti-BLG D1 scFv containing myc-tag (1:1000 dilution) was added to the wells, incubated for 1 h at room temperature. The bound D1 scFv was detected using mouse anti-myc antibody (clone 9E10, ATCC # CRL-1729) and AFOS-conjugated anti-mouse Ig antibody (Bio-Rad). As a negative control, a triple mutant of BLG (T18Y, E45Y, L57Y) was used in this assay.

This sandwich ELISA configuration shows that the recombinant BLG mutants H146P, H148P and S150P are monomeric by a concentration dependent manner. At high concentration (100 μg/ml), the BLG mutants behave like dimers, but at lower concentrations (10 μg/ml) there are monomers that could not be recognised by the sandwich ELISA in which the D1 Fab fragment was coated on the wells and D1 scFv-myc fusion was used for the detection whereas the dimeric native BLG was detected clearly still at the concentration of 10 μg/ml. This demonstrates that in high concentrations rBLG mutants form transient dimers whereas in low concentrations the BLG mutants are as monomers, thus, these cannot be recognised by the BLG-specific antibody in a sandwich-type ELISA.

Example 4

Figure 3:
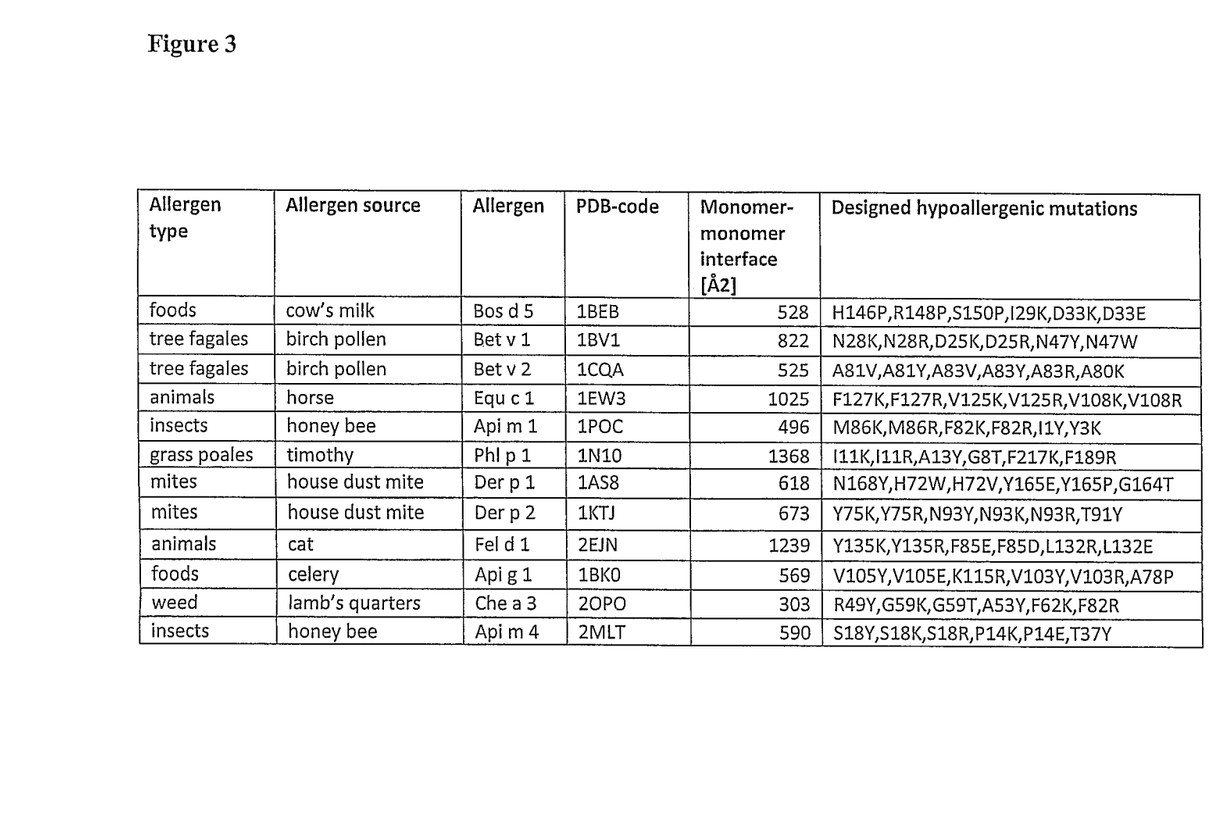
FIG. 3 An example of suggested mutants on the monomer-monomer interface of 12 symmetric allergen dimers.

The coordinates of the solved three-dimensional crystal structures of allergens Bos d 5, Bet v 1, Bet v 2, Equ c 1, Api m 1, Phl p 1, Der p 1, Der p 2, Fel d 1, Api g 1, Che a 3, and Apl m 5 were used to analyze visually allergen molecule packing by using molecular graphics software (PYMOL (DeLano 2002), O (Jones et al. 1991), and XTALVIEW (McRee, 1999)). In the analysis, the goal was to find rotational symmetry axis between allergen molecules and corresponding monomer-monomer interface (see FIG. 1). An example of suggested mutants on the found monomer-monomer interface of 12 symmetric allergen dimers are shown in FIG. 3.

TABLE I

Primers used for the PCR amplification of the monomeric BLG mutants.

A: 5'-GCGCCGACATCATAACGGTTC-3'

B: 5'-ACCTGAAGCTTAATGGTGATGGTGATGATGAATATGGCACTGTT CTTCCAGCTGGGTCGGGTTAAAGCTCAGACGAATCGGCATCGGCAGC-3'

C: 5'-ACCTGAAGCTTAATGGTGATGGTGATGATGAATATGGCACTGT TCTTCCAGCTGGGTCGGGTTAAAGCTC AGCGGAATATGCATC-3'

D: 5'-ACCTGAAGCTTAATGGTGATGGTGATGATGAATATGGCACTGT TCTTCCAGCTGGGTCGGGTTAAACGGC AGACGAATATG-3'

E: 5'-ACCTGAAGCTTAATGGTGATGGTGATGATGAATATGGCACTGTT CTTCCAGCTGGGTCGGGTTAAACGGCAGCGGAATCGGCATCGGCAGC-3'

TABLE 2

Detected monomer-monomer interfaces in allergens.

| allergen | oligomerization state | monomer-monomer interface (Å2) | PDB-code | species | common name | allergen type |
| --- | --- | --- | --- | --- | --- | --- |
| Pru p 3 | 4 | 4010 | 2B5S | Primus persica | peach | foods |
| Asp f 6 | 4 | 3360 | 1KKC | Aspergillus fumigatus | | fungi (moulds) |
| Phl p 7 | 2 | 2569 | 1K9U | Phleum pratense | timothy | grass Poales |
| Gly m lectin | 4 | 2380 | 1SBF | Glycine max | soybean | foods |
| Rat n 1 | 4 | 2334 | 2A2G | Rattus norvegius | rat (urine) | animals |
| Phl p 1 | 2 | 1368 | 1N10 | Phleum pratense | timothy | grass Poales |
| Fel d 1 | 2 | 1239 | 2EJN | Felis domesticus | cat | |
| Bla g 2 | 2 | 1149 | 1YG9 | Blattella germanica | German cockroach | insects |
| Equ c 1 | 2 | 1025 | 1EW3 | Equus caballus | domestic horse | animals |
| Mala s 13 | 2 | 994 | 2J23 | Malassezia sympodialis | | fungi |
| Bet v 1 | 2 | 822 | 1BV1 | Betula verrucosa | birch | tree Fagales |
| Bos d 4 | 2 | 761 | 1F6S | Bos domesticus | domestic cattle | foods |
| Api m 2 | 2 | 732 | 1FCU | Apis mellifera | honey bee | insects |
| Phl p 6 | 2 | 709 | 1NLX | Phleum pratense | timothy | grass Poales |
| Der p 2 | 2 | 673 | 1KTJ | Dermatophagoides pteronyssinus | European house dust mite | mites |
| Der p 1 | 2 | 616 | 2AS8 | Dermatophagoides pteronyssinus | European houst dust mite | mites |
| The I lipase | 2 | 610 | 1DT3 | Thermomyces (Humicola) lanuginosa | | |
| Api m 4 | 8 | 590 | 2MLT | Apis mellifera | honey bee | insects |
| Hev b 8 | 2 | 586 | 1G5U | Hevea brasiliensis | rubber (latex) | others |
| Api g 1 | 2 | 569 | 2BK0 | Apium graveolens | celery | foods |
| Gal d 4 | 2 | 563 | 193L | Gallus domesticus | chicken | foods |
| Phl p 5 | 2 | 542 | 1L3P | Phleum pratense | timothy | grass Poales |
| Bos d 5 | 2 | 528 | 1BEB | Bos domesticus | domestic cattle | foods |
| Bet v 2 | 2 | 525 | 1CQA | Betula verrucosa | birch | tree Fagales |
| Gal d 3 | 2 | 522 | 1AIV | Gallus domesticus | chicken | foods |
| Api m 1 | 2 | 496 | 1POC | Apis mellifera | honey bee | insects |
| Phl p 2 | 2 | 413 | 1WHO | Phleum pratense | timothy | grass Poales |
| Mus m 1 | 2 | 389 | 1MUP | Mus musculus | mouse (urine) | animals |
| Zea m 1 | 2 | 379 | 2HCZ | Zea mays | maize | pollen |
| Asp o 21 | 2 | 328 | 2GUY | Aspergillus oryzae | | fungi (moulds) |
| Che a 3 | 4 | 303 | 2OPO | Chenopodium album | lamb's-quarters | weed Caryophyllales |
| Jun a 1 | 2 | 231 | 1PXZ | Juniperus ashei | cedar | tree Cupressaceae |
| Der f 2 | 2 | 202 | 1XWV | Dermatophagoides farinae | American house dust mite | mites |
| Mala s 6 | 2 | 161 | 2CFE | Malassezia sympodialis | | fungi |
| Hev b 6.02 | 2 | 142 | 1Q9B | Hevea brasiliensis | rubber (latex) | others |

REFERENCES

Alam R & Gorska M: Lymphocytes. *J. All. Clin. Immunol.* 111 (2003) S476-S485.

André I, Bradley P, Wang C & Baker D: Prediction of the structure of symmetrical protein assemblies. *Proc. Natl. Acad. Sci. USA* 104 (2007) 17656-17661.

Bellinghausen I, Häringer B, Lafargue B, Strand D, König B, Decker H & Saloga J: Allergological implication of the quaternary hexameric structure of the cockroach allergen Per a 3. *Clin. Exp. Allergy* 38 (2007) 539-548.

Blundell T L & Srinivasan N: Symmetry, stability, and dynamics of multidomain and multicomponent protein systems. *Proc. Natl. Acad. Sci. USA* 93 (1996) 14243-14248.

Chaplin D D: Overview of the immune response. *J. All. Clin. Immunol.* 111 (2003) S442-S459.

de Halleux et al., 2005, J. Allergy Clin Immunol 117(3):571-576.

DeLano, W. L. (2002) The PyMol Molecular Graphics System (http://www.pymol.org)

Ghosh D & Gupta-Bhattacharya S: Structural insight into protein T1, the non-allergenic member of the Bet v 1 allergen family—An in silico analysis. *Mol. Immunol.* 45 (2008) 456-462.

Gould H J & Sutton B J: IgE in allergy and asthma today. *Nature Rev. Immunol.* 8 (2008) 205-217.

Jones T A, Zou J-Y, Cowan S W & Kjeldgaard: Improved methods for building protein models on electron density maps and the location of errors in these models. *Acta Crystallogr. A* 47 (1991) 110-119.

Krissinel E & Henrick K: Inference of macromolecular assemblies from crystalline state. *J. Mol. Biol.* 372 (2007) 774-797.

Kuriyan J & Eisenberg D: The origin of protein interactions and allostery in colocalization. *Nature* 450 (2007) 983-990.

Mi Li, Alla Gustchina, Jerry Alexandratos, Alexander Wlodawer, Sabina Wünschmann, Christopher L. Kepley, Martin D. Chapman, and Anna Pomes: Crystal structure of a dimerized cockroach allergen bla g 2 complexed with a monoclonal antibody. J. Biol. Chem. (2008) http://www.jbc.org/cgi/doi/10.1074/jbc.M800937200; published on Jun. 2, 2008.

McRee D E: XtalView/Xfit—a versatile program for manipulating atomic coordinates and electron density. *J. Struct. Biol.* 125 (1999) 156-165.

Niemi M, Jylhä S, Laukkanen M-L, Söderlund H, Makinen-Kiljunen S, Kallio J M, Hakulinen N, Haahtela T, Takkinen K & Rouvinen J: Molecular interactions between a recombinant IgE antibody and the β-lactoglobulin allergen. *Structure*, 15 (2007) 1413-1421.

Nooren I M A & Thornton J M: Structural characterization and functional significance of transient protein-protein interactions. *J. Mol. Biol.* 325 (2003) 991-1018.

Pauli G, Purohit A, Oster J-P, de Blay F, Vrtala S, Niederberger V, Kraft D & Valenta R: Comparison of genetically engineered hypoallergenic rBet v 1 derivatives with rBet v 1 wild-type by skin prick and intradermal testing: results obtained in a French population. *Clin. Exp. Allergy* 30 (2000) 1076-1084.

Prussin C & Metcalfe D D: IgE, mast cells, basophils, and eosinophils. *J. All. Clin. Immunol.* 111 (2003) S486-S494.

Sakurai K, and Goto, Y. Manipulating monomer-dimer equilibrium of bovine β-lactoglobulin by amino acid substitution. *J. Biol. Chem.* 277 (2002) 25735-25740.

Schöll I, Kalkura N, Shedziankova Y, Bergmann A, Verdino P, Knittelfelder R, Kopp T, Hantusch B, Betzel C, Dierks K, Scheiner O, Boltz-Nitulescu G, Keller W & Jensen-Jarolim E: Dimerization of the major birch pollen allergen Bet v 1 is important for its In vivo IgE-cross-linking potential in mice. *J. Immunol.* 175 (2005) 6645-6650.

Van Hage-Hamsten M, Kronqvist M, Zetterström O, Johansson E, Niederberger V, Vrtala S, Grönlund H, Grönneberg R & Valenta R: Skin test evaluation of genetically engineered hypoallergenic derivatives of the major birch pollen allergen, Bet v 1: Results obtained with a mix of two recombinant Bet v 1 fragments and recombinant Bet v 1 trimer in a Swedish population before the birch pollen season. *J. Allergy Clin. Immunol.* 104 (1999) 969-977.

Verdino P, Westritschnig K, Valenta R & Keller W: The cross-reactive calcium-binding pollen allergen, Phl p 7, reveals a novel dimer assembly. *EMBO J.* 21 (2002) 5007-5016.

Vrtala S, Hirtenlehner K, Vangelista L, Pastore A, Eichler H G, Sperr W R, Valent P, Ebner C, Kraft D & Valenta R: Conversion of the major birch pollen allergen, Bet v 1, into two nonanaphylactic T cell epitope-containing fragments: candidates for a novel form of specific immunotherapy. *J. Clin. Invest.* 99 (1997) 1673-1681.

The invention claimed is:

1. Method for preparing a hypoallergen candidate for immunotherapy comprising the steps of:
   (a) altering monomer-monomer interface area of an allergenic polypeptide, wherein said monomer-monomer interface area is about or less than 850 Å$^2$ and is related to the formation of transient dimers or oligomers in order to inactivate or reduce the polypeptide's natural ability to form transient dimers or oligomers, and wherein said allergenic polypeptide is selected from the group consisting of Bet v 2, Api m 1, Der p 2, Api g 1, Che a 3, Api m 5, Phl p 6, Hev b 8, Gal d 4, Phl p 5, Gal d 3, Phl p 2, Mus m 1, Zea m 1, and Asp o 21; and
   (b) testing in vitro the altered polypeptide obtained from step (a) for ability to activate release of histamine or other mediators of an allergic reactions from human cells checking that a IgE antibody specific to said allergenic polypeptide still binds to the altered polypeptide obtained from step (a) to confirm that said allergenic polypeptide has a native-like structure and thus capability to prevent the crosslinking of the IgE-FcεRI complexes on a mast cell or basophile surface antibodies and immunogenic potential to develop protective IgG antibodies, wherein those altered polypeptides which do not activate histamine release or said other mediators or activate histamine release or said other mediators less than the parent polypeptide and which have said native-like structure are considered as hypoallergen candidates for immunotherapy.

2. The method according to claim 1 further comprising a step of administering a pharmaceutically effective amount of the altered polypeptide obtained from step (a) or (b) to a patient suffering from an allergy.

3. The method according to claim 1, wherein the human cells used in step b) are leukocytes or mast cells.

4. The method according to claim 1, wherein in step a) the surface area of said polypeptide related to the formation of dimers or oligomers is altered by directed mutagenesis of the nucleic acid encoding said polypeptide.

5. The method according to claim 4, wherein directed mutagenesis is used to produce amino acid substitutions to said polypeptide.

6. The method according to claim 5, wherein said substitutions are changes from small residues to larger ones or from hydrophobic residues to hydrophilic residues or altering the structure of polypeptide main chain.

7. The method according to claim 1, wherein said allergenic polypeptide is selected from the group consisting of: Bet v 2, Api m 1, Der p 2, Api g 1, Che a 3, and Api m 5.

8. The method according to claim 1, wherein said allergenic polypeptide is β-lactoglobulin.

9. The method according to claim 1, wherein said allergenic polypeptide is selected from the group consisting of: Phl p 6, Hey b 8, Gal d 4, Phl p 5, Gal d 3, Phl p 2, Mus m 1, Zea m 1, and Asp o 21.

10. Method for preparing a hypoallergen candidate for immunotherapy comprising the steps of:
    (a) analysing by computational analyses the coordinates of solved three-dimensional allergen structure to confirm the presence of rotational symmetry axis between monomers of an allergenic polypeptide selected from the group consisting of Bet v 2, Api m1, Der p 2, Api g 1, Che a 3, Api m 5, Phl p 6, Hey b 8, Gal d 4, Phl p 5, Gal d 3, Phl p 2, Mus m 1, Zea m 1, and Asp o 21, wherein said monomer-monomer interface has an area about or less than 850 Å$^2$, and wherein the monomer-monomer interface is searched for amino acid residues the substitution of which would hinder the transient dimer formation;
    (b) altering the monomer-monomer interface area of said polypeptide in order to inactivate or reduce the polypeptide's natural ability to form transient dimers or oligomers; and
    (c) testing in vitro the altered polypeptide obtained from step (b) for ability to activate release of histamine or other mediators of an allergic reactions from human cells and checking that an IgE antibody specific to said allergenic polypeptide still binds to the altered polypeptide obtained from step (b) to confirm that said allergenic polypeptide has a native-like structure and thus is capable of preventing the crosslinking of the IgE-FcεRI complexes on a mast cell or basophile surface antibodies and immunogenic potential to develop protective IgG antibodies, wherein those altered polypeptides which do not activate histamine release or said other mediators or activate histamine release or said other mediators less than the parent polypeptide and which have said native-like structure are considered as hypoallergen candidates for immunotherapy.

* * * * *

SEQUENCE LISTING

```
<160> NUMBER OF SEQ ID NOS: 4

<210> SEQ ID NO 1
<211> LENGTH: 162
<212> TYPE: PRT
<213> ORGANISM: Bos taurus
<220> FEATURE:
<221> NAME/KEY: MISC_FEATURE
<223> OTHER INFORMATION: Amino acid sequence of recombinant H146P beta-
      lactoglobulin

<400> SEQUENCE: 1

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
            20                  25                  30

Asp Ala Gln Ser Ala Pro Leu Arg Val Tyr Val Glu Glu Leu Lys Pro
        35                  40                  45
```

```
Thr Pro Glu Gly Asp Leu Glu Ile Leu Leu Gln Lys Trp Glu Asn Gly
         50                  55                  60

Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
                100                 105                 110

Pro Glu Gln Ser Leu Ala Cys Gln Cys Leu Val Arg Thr Pro Glu Val
             115                 120                 125

Asp Asp Glu Ala Leu Glu Lys Phe Asp Lys Ala Leu Lys Ala Leu Pro
         130                 135                 140

Met Pro Ile Arg Leu Ser Phe Asn Pro Thr Gln Leu Glu Glu Gln Cys
145                 150                 155                 160

His Ile

<210> SEQ ID NO 2
<211> LENGTH: 162
<212> TYPE: PRT
<213> ORGANISM: Bos taurus
<220> FEATURE:
<221> NAME/KEY: MISC_FEATURE
<223> OTHER INFORMATION: Amino acid sequence of recombinant R148P beta-
      lactoglobulin

<400> SEQUENCE: 2

Leu Ile Val Thr Gln Thr Met Lys Gly Leu Asp Ile Gln Lys Val Ala
 1               5                  10                  15

Gly Thr Trp Tyr Ser Leu Ala Met Ala Ala Ser Asp Ile Ser Leu Leu
                 20                  25                  30

Asp Ala Gln Ser Ala Pro Leu Arg Val Tyr Val Glu Glu Leu Lys Pro
             35                  40                  45

Thr Pro Glu Gly Asp Leu Glu Ile Leu Leu Gln Lys Trp Glu Asn Gly
         50                  55                  60

Glu Cys Ala Gln Lys Lys Ile Ile Ala Glu Lys Thr Lys Ile Pro Ala
 65                  70                  75                  80

Val Phe Lys Ile Asp Ala Leu Asn Glu Asn Lys Val Leu Val Leu Asp
                 85                  90                  95

Thr Asp Tyr Lys Lys Tyr Leu Leu Phe Cys Met Glu Asn Ser Ala Glu
                100                 105                 110

Pro Glu Gln Ser Leu Ala Cys Gln Cys Leu Val Arg Thr Pro Glu Val
             115                 120                 125

Asp Asp Glu Ala Leu Glu Lys Phe Asp Lys Ala Leu Lys Ala Leu Pro
         130                 135                 140

Met His Ile Pro Leu Ser Phe Asn Pro Thr Gln Leu Glu Glu Gln Cys
145                 150                 155                 160

His Ile

<210> SEQ ID NO 3
<211> LENGTH: 162
<212> TYPE: PRT
<213> ORGANISM: Bos taurus
<220> FEATURE:
<221> NAME/KEY: MISC_FEATURE
<223> OTHER INFORMATION: Amino acid sequence of recombinant S150P beta-
      lactoglobulin

<400> SEQUENCE: 3
```

```
Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
                20                  25                  30

Asp Ala Gln Ser Ala Pro Leu Arg Val Tyr Val Glu Glu Leu Lys Pro
            35                  40                  45

Thr Pro Glu Gly Asp Leu Glu Ile Leu Leu Gln Lys Trp Glu Asn Gly
        50                  55                  60

Glu Cys Ala Gln Lys Lys Ile Ile Ala Glu Lys Thr Lys Ile Pro Ala
65                  70                  75                  80

Val Phe Lys Ile Asp Ala Leu Asn Glu Asn Lys Val Leu Val Leu Asp
                85                  90                  95

Thr Asp Tyr Lys Lys Tyr Leu Leu Phe Cys Met Glu Asn Ser Ala Glu
                100                 105                 110

Pro Glu Gln Ser Leu Ala Cys Gln Cys Leu Val Arg Thr Pro Glu Val
            115                 120                 125

Asp Asp Glu Ala Leu Glu Lys Phe Asp Lys Ala Leu Lys Ala Leu Pro
        130                 135                 140

Met His Ile Arg Leu Pro Phe Asn Pro Thr Gln Leu Glu Glu Gln Cys
145                 150                 155                 160

His Ile

<210> SEQ ID NO 4
<211> LENGTH: 162
<212> TYPE: PRT
<213> ORGANISM: Bos taurus
<220> FEATURE:
<221> NAME/KEY: MISC_FEATURE
<223> OTHER INFORMATION: Amino acid sequence of recombinant H146P/R148P/
      S150P (triple mutant) beta-lactoglobulin

<400> SEQUENCE: 4

Leu Ile Val Thr Gln Thr Met Lys Gly Leu Asp Ile Gln Lys Val Ala
1               5                   10                  15

Gly Thr Trp Tyr Ser Leu Ala Met Ala Ala Ser Asp Ile Ser Leu Leu
                20                  25                  30

Asp Ala Gln Ser Ala Pro Leu Arg Val Tyr Val Glu Glu Leu Lys Pro
            35                  40                  45

Thr Pro Glu Gly Asp Leu Glu Ile Leu Leu Gln Lys Trp Glu Asn Gly
        50                  55                  60

Glu Cys Ala Gln Lys Lys Ile Ile Ala Glu Lys Thr Lys Ile Pro Ala
65                  70                  75                  80

Val Phe Lys Ile Asp Ala Leu Asn Glu Asn Lys Val Leu Val Leu Asp
                85                  90                  95

Thr Asp Tyr Lys Lys Tyr Leu Leu Phe Cys Met Glu Asn Ser Ala Glu
                100                 105                 110

Pro Glu Gln Ser Leu Ala Cys Gln Cys Leu Val Arg Thr Pro Glu Val
            115                 120                 125

Asp Asp Glu Ala Leu Glu Lys Phe Asp Lys Ala Leu Lys Ala Leu Pro
        130                 135                 140

Met Pro Ile Pro Leu Pro Phe Asn Pro Thr Gln Leu Glu Glu Gln Cys
145                 150                 155                 160

His Ile
```